United States Patent
Finlay et al.

(10) Patent No.: US 8,048,094 B2
(45) Date of Patent: *Nov. 1, 2011

(54) SIMULTANEOUS PROPORTIONAL CONTROL OF SURGICAL PARAMETERS IN A MICROSURGICAL SYSTEM

(75) Inventors: Russell L. Finlay, Keller, TX (US); Christopher C. Jung, Mission Viego, CA (US); John C. Huculak, Mission Viejo, CA (US); Paul Essex, Rancho Santa Margarita, CA (US); Kirk W. Todd, Yorba Linda, CA (US)

(73) Assignee: Novartis AG, Basel (CH)

( * ) Notice: Subject to any disclaimer, the term of this patent is extended or adjusted under 35 U.S.C. 154(b) by 392 days.

This patent is subject to a terminal disclaimer.

(21) Appl. No.: 12/277,713

(22) Filed: Nov. 25, 2008

(65) Prior Publication Data

US 2009/0082794 A1    Mar. 26, 2009

Related U.S. Application Data

(63) Continuation of application No. 10/234,863, filed on Sep. 4, 2002, now Pat. No. 7,470,277.

(60) Provisional application No. 60/329,904, filed on Oct. 16, 2001.

(51) Int. Cl.
  *A61B 17/32* (2006.01)
(52) U.S. Cl. .......... 606/166; 606/1; 606/170; 200/86.5
(58) Field of Classification Search .......... 606/1, 107, 606/166, 167, 169, 170, 178
See application file for complete search history.

(56) References Cited

U.S. PATENT DOCUMENTS

| | | |
|---|---|---|
| 3,884,238 A | 5/1975 | O'Malley et al. |
| 4,168,707 A | 9/1979 | Douvas et al. |
| 4,493,698 A | 1/1985 | Wang et al. |
| 4,577,629 A | 3/1986 | Martinez |
| 4,696,298 A | 9/1987 | Higgins et al. |
| 4,757,814 A | 7/1988 | Wang et al. |
| 4,758,220 A | 7/1988 | Sundblom et al. |
| 4,768,506 A | 9/1988 | Parker et al. |
| 4,770,654 A | 9/1988 | Rogers et al. |
| 4,790,816 A | 12/1988 | Sundblom et al. |
| 4,810,242 A | 3/1989 | Sundblom et al. |
| 4,819,635 A | 4/1989 | Shapiro |
| 4,837,857 A | 6/1989 | Scheller et al. |
| 4,841,984 A | 6/1989 | Armeniades et al. |

(Continued)

FOREIGN PATENT DOCUMENTS

WO    9613845 A1    5/1996

(Continued)

OTHER PUBLICATIONS

Japanese patent abstract; Publication No. 2000-229102, published Aug. 22, 2000.

*Primary Examiner* — Darwin Erezo
(74) *Attorney, Agent, or Firm* — W. David Lee

(57) ABSTRACT

A microsurgical system, and a foot controller for the improved operation of a microsurgical system, are disclosed. A surgeon may use the foot controller to simultaneously control multiple surgical parameters based upon movement of a foot pedal of the foot controller in a single plane of motion.

6 Claims, 5 Drawing Sheets

U.S. PATENT DOCUMENTS

| | | | |
|---|---|---|---|
| 4,850,377 | A | 7/1989 | Parker et al. |
| 4,909,249 | A | 3/1990 | Akkas et al. |
| 4,940,468 | A | 7/1990 | Petillo |
| 4,983,901 | A | 1/1991 | Lehmer |
| 4,986,827 | A | 1/1991 | Akkas et al. |
| 5,019,035 | A | 5/1991 | Missirlian et al. |
| 5,020,535 | A | 6/1991 | Parker et al. |
| 5,024,652 | A | 6/1991 | Dumenek et al. |
| 5,047,008 | A | 9/1991 | de Juan, Jr. et al. |
| 5,059,204 | A | 10/1991 | Lawson et al. |
| 5,061,238 | A | 10/1991 | Shuler |
| 5,091,056 | A | 2/1992 | Autio |
| 5,157,603 | A | 10/1992 | Scheller et al. |
| 5,176,628 | A | 1/1993 | Charles et al. |
| 5,268,624 | A | 12/1993 | Zanger |
| 5,284,472 | A | 2/1994 | Sussman et al. |
| 5,342,293 | A | 8/1994 | Zanger |
| 5,354,268 | A | 10/1994 | Peterson et al. |
| 5,380,280 | A | 1/1995 | Peterson |
| 5,423,844 | A | 6/1995 | Miller |
| 5,455,766 | A | 10/1995 | Scheller et al. |
| 5,474,532 | A | 12/1995 | Steppe |
| 5,520,652 | A | 5/1996 | Peterson |
| 5,554,894 | A | 9/1996 | Sepielli |
| 5,580,347 | A | 12/1996 | Reimels |
| 5,630,827 | A | 5/1997 | Vijfvinkel |
| 5,674,194 | A | 10/1997 | Jung et al. |
| 5,733,297 | A | 3/1998 | Wang |
| 5,782,849 | A | 7/1998 | Miller |
| 5,810,765 | A | 9/1998 | Oda |
| 5,833,643 | A | 11/1998 | Ross et al. |
| 5,873,885 | A | 2/1999 | Weidenbenner |
| 5,910,139 | A | 6/1999 | Cochran et al. |
| 5,983,749 | A | 11/1999 | Holtorf |
| 6,010,496 | A | 1/2000 | Appelbaum et al. |
| 6,179,829 | B1 | 1/2001 | Bisch et al. |
| 6,452,120 | B1 | 9/2002 | Chen |
| 6,452,123 | B1 | 9/2002 | Chen |
| 6,514,268 | B2 | 2/2003 | Finlay et al. |
| 6,629,986 | B1 | 10/2003 | Ross et al. |
| 6,659,998 | B2 | 12/2003 | DeHoogh et al. |
| 6,773,445 | B2 | 8/2004 | Finlay et al. |
| 6,962,581 | B2 | 11/2005 | Thoe |
| 7,470,277 | B2 * | 12/2008 | Finlay et al. .................. 606/166 |

FOREIGN PATENT DOCUMENTS

| | | | |
|---|---|---|---|
| WO | | 9808442 A1 | 3/1998 |
| WO | | 9914648 A1 | 3/1999 |
| WO | | 0012037 A1 | 3/2000 |

* cited by examiner

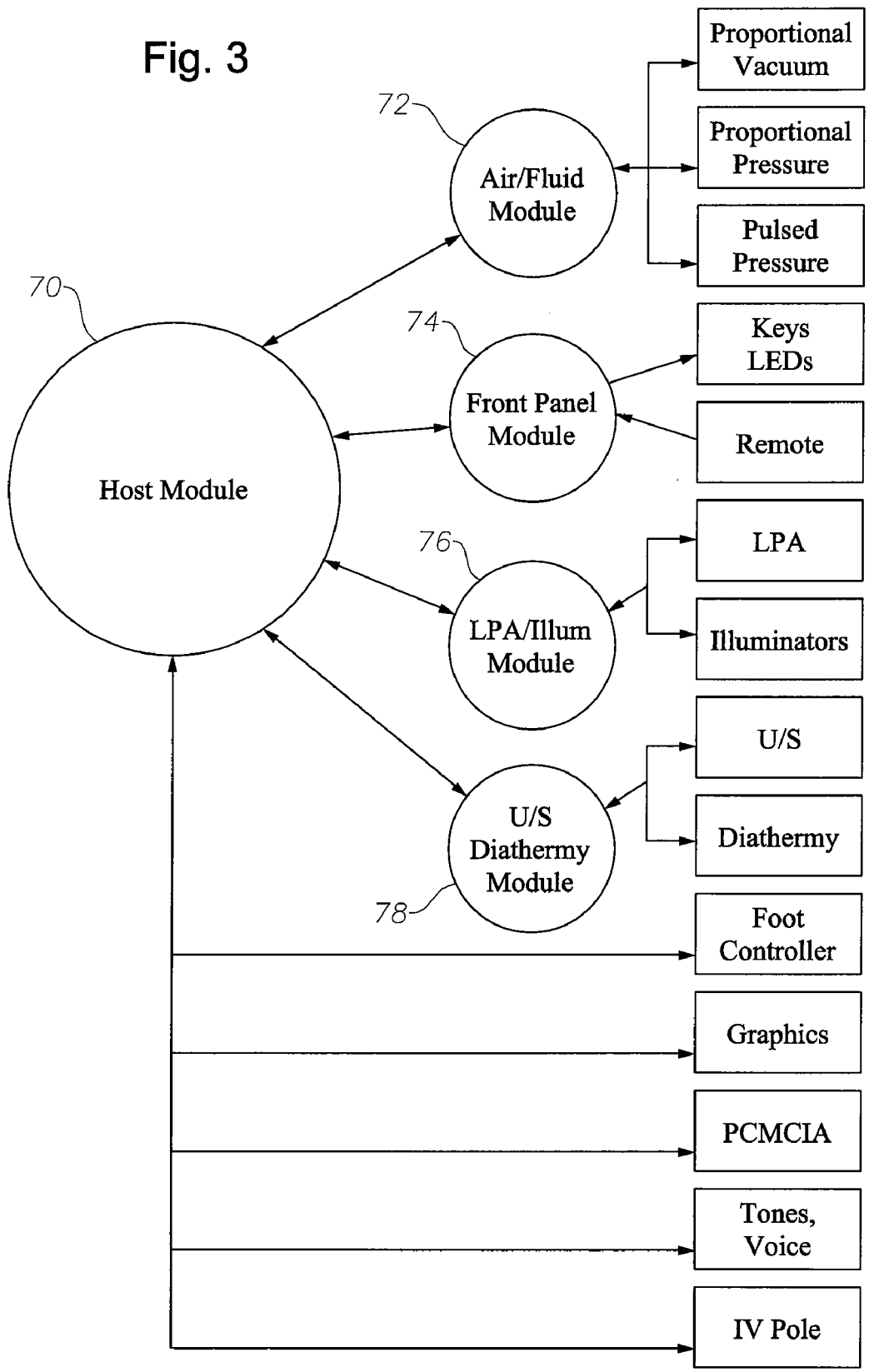

SIMULTANEOUS PROPORTIONAL CONTROL OF SURGICAL PARAMETERS IN A MICROSURGICAL SYSTEM

This application is a continuation of U.S. application Ser. No. 10/234,863, filed Sep. 4, 2002, now U.S. Pat. No. 7,470,277 which claims the priority of U.S. Provisional Application No. 60/329,904, filed Oct. 16, 2001.

FIELD OF THE INVENTION

The present invention generally pertains to microsurgical systems. More particularly, but not by way of limitation, the present invention pertains to foot controllers for the operation of such systems, as well as using such foot controllers to simultaneously control multiple surgical parameters based upon movement of a foot pedal of the foot controller in a single plane of motion.

DESCRIPTION OF THE RELATED ART

Various foot controllers are used to control microsurgical systems, and particularly ophthalmic microsurgical systems. During ophthalmic surgery, a surgeon views the patient's eye through an operating microscope. To control the microsurgical system and its associated handpieces during the various portions of the surgical procedure, the surgeon must either instruct a nurse how to alter the machine settings on the surgical system, or use the foot controller to change such settings. Where possible, many surgeons prefer to use the foot controller to alter the machine settings on the surgical system, eliminating the need to converse with a nurse during the surgical procedure.

The challenge of controlling two surgical parameters of a surgical system or its associated handpiece during an ophthalmic surgical procedure has been addressed in different ways. One method is using a foot controller with a vertical range of motion to control one surgical parameter (e.g. cut rate) while holding the second surgical parameter (e.g. aspiration flow rate) at a preset value input on the user interface of the surgical console. This implementation requires the surgeon to switch the mode of operation of the surgical console via the user interface to manipulate the magnitude of the second parameter. Therefore, to manipulate the second parameter, the surgeon must either interrupt the surgical procedure or instruct a nurse on how to manipulate the second parameter. Another method is using two separate foot controllers, each having a vertical range of motion, to provide linear control of two different surgical parameters. Each foot controller is dedicated to a single parameter. However, the simultaneous motion of both feet necessary to effect a coordinated surgical outcome has proven to be complex to learn and difficult for the surgeon to reliably control. Another method is using a foot controller with the capability to provide linear control of one surgical variable in a vertical range of motion ("pitch") simultaneous with linear control of a second surgical variable in a horizontal range of motion ("yaw"). This approach is disclosed in International Publication Number WO 98/08442. However, managing pitch and yaw simultaneously requires a significant amount of dexterity and is difficult for many surgeons to perform. Several patents and published patent applications have addressed these traditional methods and similar methods. Examples include International Publication Number WO 00/12037; International Publication Number WO 99/14648; International Publication Number WO 98/08442; International Publication No. WO 96/13845; U.S. Pat. No. 5,983,749; U.S. Pat. No. 5,580,347; U.S. Pat. No. 4,837,857; U.S. Pat. No. 4,983,901; U.S. Pat. No. 5,091,056; U.S. Pat. No. 5,268,624; U.S. Pat. No. 5,554,894; U.S. Pat. No. 4,837,857; U.S. Pat. No. 5,157,603; U.S. Pat. No. 5,342,293; U.S. Pat. No. 6,179,829; and Japanese Patent Application Publication No. 2000-229102, all of which are incorporated herein by reference.

Despite the above-described methods of control, surgeons desire a more flexible, easier to use method of actuating a foot controller to simultaneously control multiple surgical parameters in an ophthalmic surgical procedure. The present invention is directed to a microsurgical system and foot controller that provide such flexibility.

SUMMARY OF THE INVENTION

In a preferred embodiment, the present invention comprises a method of providing simultaneous proportional control of multiple surgical parameters in a microsurgical system. The microsurgical system has a computer, a foot controller operatively coupled to the computer, a first surgical parameter, and a second surgical parameter. The foot controller has a foot pedal capable of movement in a single plane of motion between a first end point and a second end point. A position of the foot pedal between the first end point and the second end point is determined. A value of the first surgical parameter is proportionally controlled as a function of the position of the foot pedal, and a value of the second surgical parameter is proportionally controlled as a function of the position of the foot pedal simultaneous with proportionally controlling the value of the first surgical parameter.

BRIEF DESCRIPTION OF THE DRAWINGS

For a more complete understanding of the present invention, and for further objects and advantages thereof, reference is made to the following description taken in conjunction with the accompanying drawings in which:

FIG. 3 is a block diagram of the preferred hardware and software configuration for the microsurgical system of FIG. 1;

DETAILED DESCRIPTION OF THE PREFERRED EMBODIMENTS

The preferred embodiments of the present invention and their advantages are best understood by referring to FIGS. 1 through 8 of the drawings, like numerals being used for like and corresponding parts of the various drawings.

Figure 1:
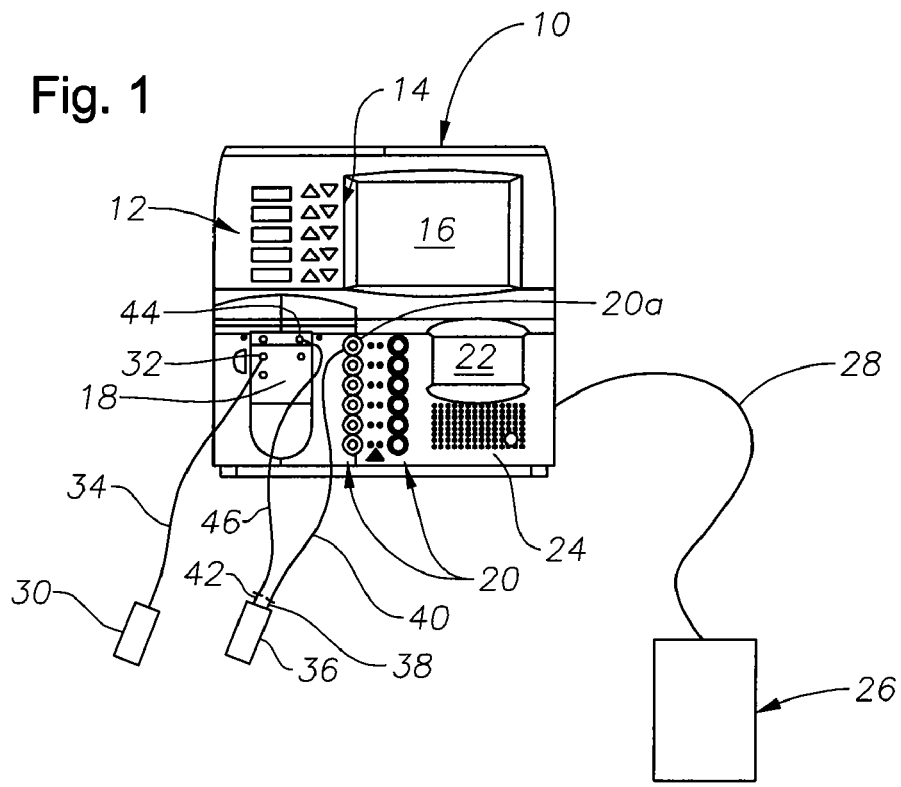
FIG. 1 is a front, schematic view of a microsurgical system according to a preferred embodiment of the present invention configured for posterior segment ophthalmic surgery.

FIG. 1 shows a microsurgical system 10 according to a preferred embodiment of the present invention. As shown in FIG. 1, microsurgical system 10 is an ophthalmic microsurgical system. However, microsurgical system 10 may be any microsurgical system, including a system for performing otic, nasal, throat, or other surgeries. System 10 is capable of providing ultrasound power, irrigation fluid, and aspiration vacuum to a ultrasonic handpiece in an anterior segment ophthalmic surgical procedure. System 10 is also capable of providing pneumatic drive pressure and aspiration vacuum to a vitrectomy probe and irrigation fluid to an infusion cannula is a posterior segment ophthalmic surgical procedure. A preferred surgical system 10 is the Accurus® surgical system available from Alcon Laboratories, Inc. of Fort Worth, Tex.

Figure 1A:
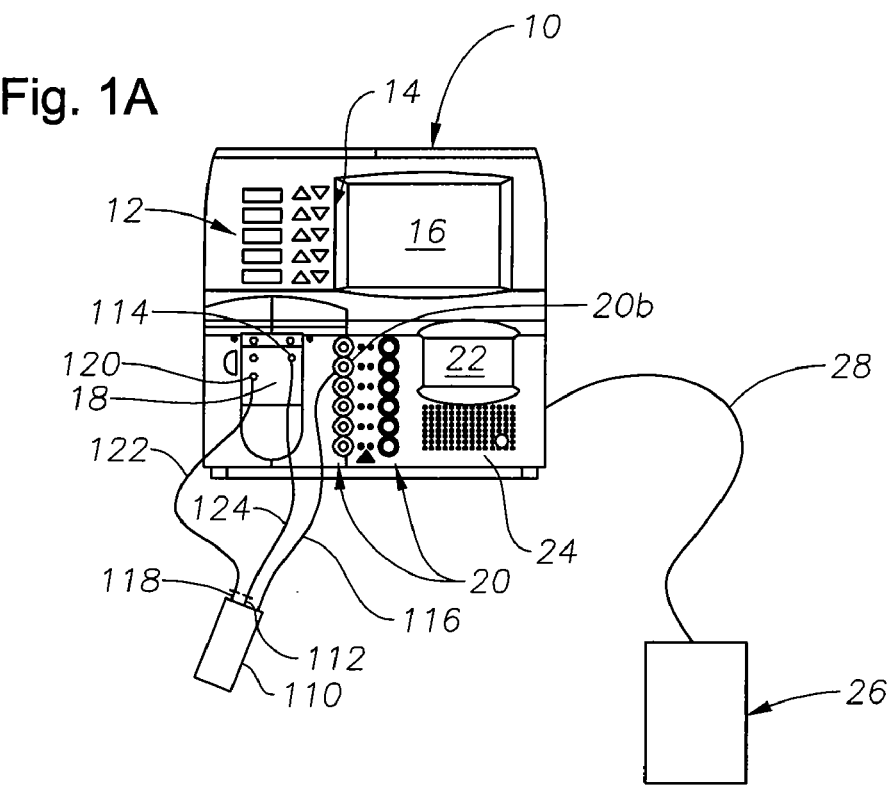
FIG. 1A is a front, schematic view of the microsurgical system of FIG. 1 configured for anterior segment ophthalmic surgery.

System 10 preferably also includes a series of light emitting diode ("LED") displays 12 for displaying system parameters, a series of "up/down" arrows keys 14 for altering the system parameters displayed on LED displays 12, a liquid crystal display ("LCD") 16 with touch screen capability, a surgical cassette 18, a series of electrical and pneumatic connectors or ports 20 for operatively coupling with the various surgical handpieces associated with system 10, an illuminator module 22, and a speaker 24. A foot controller 26 is operatively coupled to system 10 via conventional electronic cable 28. As mentioned above, a series of handpieces are operatively coupled to system 10 during ophthalmic surgery. Exemplary handpieces utilized in anterior segment ophthalmic surgery include an irrigation handpiece, an irrigation/aspiration handpiece, an ultrasonic handpiece, and/or a diathermy handpiece. A preferred ultrasonic handpiece is a phacoemulsification handpiece. By way of example, FIG. 1A shows a phacoemulsification handpiece 110 operatively coupled to system 10. Irrigation port 112 of handpiece 110 is fluidly coupled to irrigation outlet 114 of surgical cassette 18 via conventional medical grade flexible tubing 116. Aspiration port 118 of handpiece 110 is fluidly coupled to aspiration port 120 of cassette 18 via conventional medical grade flexible tubing 122. Handpiece 110 is powered by electronic cable 124, which is coupled to ultrasound drive port 20b of system 10. Exemplary handpieces utilized in posterior segment ophthalmic surgery include an extrusion handpiece, an infusion cannula, a victrectomy probe, microsurgical scissors, and/or a diathermy handpiece. By way of example, in FIG. 1 an infusion cannula 30 is shown fluidly coupled to an irrigation outlet 32 of surgical cassette 18 via conventional medical grade flexible tubing 34. Also by way of example, FIG. 1 shows a vitrectomy probe 36 operatively coupled to system 10. Pneumatic drive port 38 of probe 36 is fluidly coupled to pneumatic pressure port 20a of system 10 via conventional medical grade flexible tubing 40. Aspiration port 42 of probe 36 is fluidly coupled to an aspiration port 44 of cassette 18 via conventional medical grade flexible tubing 46.

Figure 2:
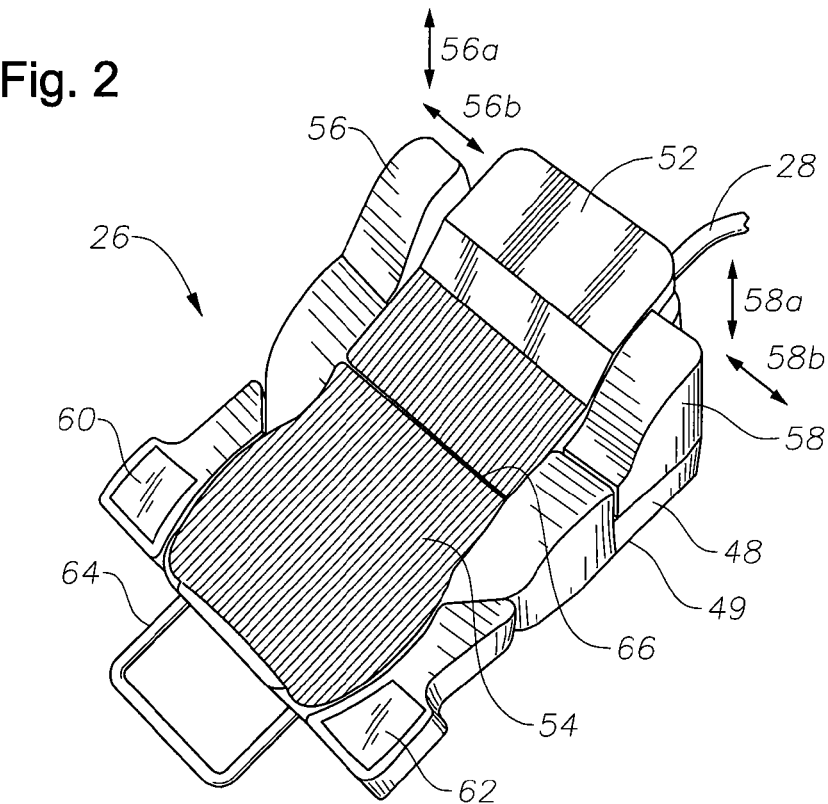
FIG. 2 is perspective view of a preferred embodiment of a foot controller for the microsurgical system of FIG. 1.

FIG. 2 shows a front, perspective view of a preferred embodiment of foot controller 26. Foot controller 26 has a body 48 with a base 49 that supports foot controller 26 on the operating room floor. Body 48 preferably includes a foot pedal 52, a heel rest 54, a left toe switch 56, a right toe switch 58, a left heel switch 60, a right heel switch 62, and a handle 64.

Foot pedal 52 is rotationally coupled to body 48 along line 66. Foot pedal 52 may be depressed using the upper portion of a surgeon's foot to move from a fully undepressed position, as shown in FIG. 2, to a fully depressed position in which foot pedal 52 lies in generally the same plane as heel rest 54. The plane of heel rest 54 is preferably disposed at an angle relative to the plane of base 49 to increase surgeon comfort. Alternatively, the plane of heel rest 54 may be parallel to the plane of base 49, if desired. Foot pedal 52 is used by the surgeon to provide proportional control to certain functions of microsurgical system 10. By way of example, depending on the operating mode of system 10, foot pedal 10 may be used to provide proportional control of vitrectomy probe cut rate, vitrectomy probe aspiration vacuum, ultrasound handpiece power, or ultrasound handpiece aspiration flow rate.

Left toe switch 56 is a dual mode binary switch. The first mode of switch 56 is actuated when a surgeon presses downward on switch 56 with his or her toe. This first mode is referred to herein as left vertical switch 56a. The second mode of switch 56 is actuated when a surgeon presses in a generally outward, horizontal direction on switch 56 with the side of his or her foot. This second mode is referred to herein as left horizontal switch 56b. Switch 56 is preferably a momentary actuation type switch that provides tactile feedback to the user. Switch 56 is preferably constructed using two Part Number P3-30125 switches available from Otto Controls of Carpenterville, Ill., one for left vertical switch 56a, and a second for left horizontal switch 56b.

Right toe switch 58 is also a dual mode binary switch. The first mode of switch 58 is actuated when a surgeon presses downward on switch 58 with his or her toe. This first mode is referred to herein as right vertical switch 58a. The second mode of switch 58 is actuated when a surgeon presses in a generally outward, horizontal direction on switch 58 with the side of his or her foot. This second mode is referred to herein as right horizontal switch 58b. Switch 58 is preferably a momentary actuation type switch that provides tactile feedback to the user, and is preferably constructed in the same manner as switch 56.

Left heel switch 60 is a binary switch that is actuated when a surgeon presses downward with his or her heel. Right heel switch 62 is a binary switch that is actuated when a surgeon presses downward with his or her heel. Switches 60 and 62 are preferably momentary actuation type switches that provide tactile feedback to the user. Switches 60 and 62 are each preferably constructed using a Part Number P3-30125 switch available from Otto Controls of Carpenterville, Ill.

Foot controller 26 may be made using conventional technology. Foot controller 26 is preferably similar in construction to the foot controller sold with the Accurus® surgical system available from Alcon Laboratories, Inc. of Fort Worth, Tex.

FIG. 3 is a high-level block diagram of the preferred hardware and software configuration of microsurgical system 10. System 10 preferably includes a Host module 70, an Air/Fluid module 72, a Front Panel module 74, a Low Pressure Air ("LPA")/Illumination module 76, and an Ultrasound ("U/S")/Diathermy module 78. Host module 70 is preferably personal computer based, and modules 72, 74, 76, and 78 are each preferably a microcontroller. Host module 70 and modules 72 through 78 preferably communicate with each other over dedicated serial lines. The hardware configuration of system 10 is preferably a star topology.

Host module 70 software communicates with each of modules 72 through 78 to maintain system 10 status, to direct system 10 functionality, and to mitigate hazard conditions. Host module 70 software also monitors and controls foot controller 26, including each of the binary switches of controller 26; displays graphics and data on display 16; monitors and controls PCMCIA card access; generates audio tones and voices for speaker 24; and controls the motorized IV pole (not shown) of system 10. The PCMCIA card is used to upload and download software into system 10.

Air/Fluid module 72 software controls the proportional vacuum source, proportional pressure source, and pulsed pressure source of system 10. Front panel module 74 software creates screens for display 16, scans for presses of keys 14 or the buttons or arrows on the touch screen of display 16, receives remote control input, and outputs LED displays 12. Screens for display 16 are created using a conventional software such as Zinc available from Wind River of Alameda, Calif. The LPA/Illumination module 76 software controls the low pressure air source of system 10 and the illuminators stored in illuminator module 22. U/S/Diathermy module 78 software controls ultrasonic power and diathermy handpiece voltage.

Figure 4:
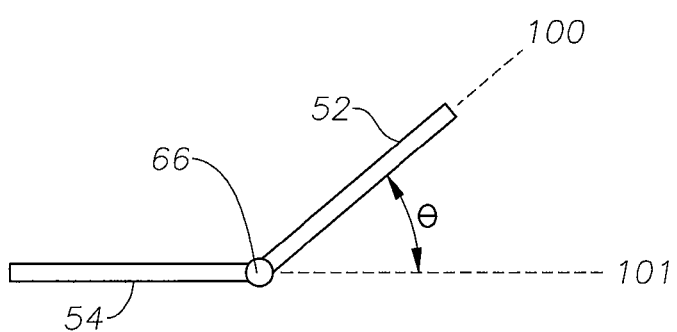
FIG. 4 is a schematic, side view of the foot pedal of the foot controller of FIG. 2 in a fully undepressed position.
Figure 5:
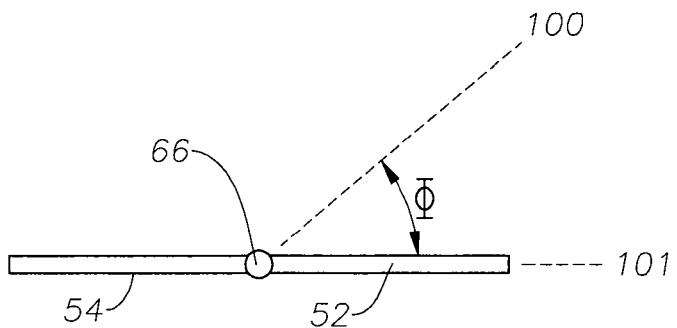
FIG. 5 is a schematic, side view of the foot pedal of the foot controller of FIG. 2 in a fully depressed position.

As shown schematically in FIG. 4, foot pedal 52 preferably forms an angle θ with the plane 101 of heel rest 54 when foot pedal 52 is in its fully undepressed position. Angle θ is preferably sub-divided into one hundred equal increments or positions Φ. Position Φ thus expresses the particular angular location of foot pedal 52 as a percentage of the total range of motion of foot pedal 52. Using conventional software, host module 70 monitors the position Φ of foot pedal 52 relative to a reference plane 100, which is coplanar with foot pedal 52 when it is in its fully undepressed position. Therefore, in a fully undepressed position of foot pedal 52, Φ is zero percent. In a fully depressed position of foot pedal 52, as shown schematically in FIG. 5, Φ is one hundred percent. Although foot pedal 52 preferably has a vertical range of motion ("pitch") as shown in FIGS. 2, 4, and 5, foot controller 26 may be designed so that foot pedal 52 has a horizontal range of motion ("yaw"), or with any other range of motion having a single plane of motion. Because foot pedal 52 can only be moved in an upward or downward direction in a single plane of motion, a surgeon may easily operate foot pedal 52, even during a lengthy surgical procedure.

According to the present invention, host module 70, and/or modules 72, 74, 76, and 78, may provide simultaneous, proportional control of two or more surgical parameters of microsurgical system 10, each as a function of position Φ of foot pedal 52. In either the anterior segment mode or the posterior segment mode, it is believed that such control yields optimum performance of system 10.

Figure 6:
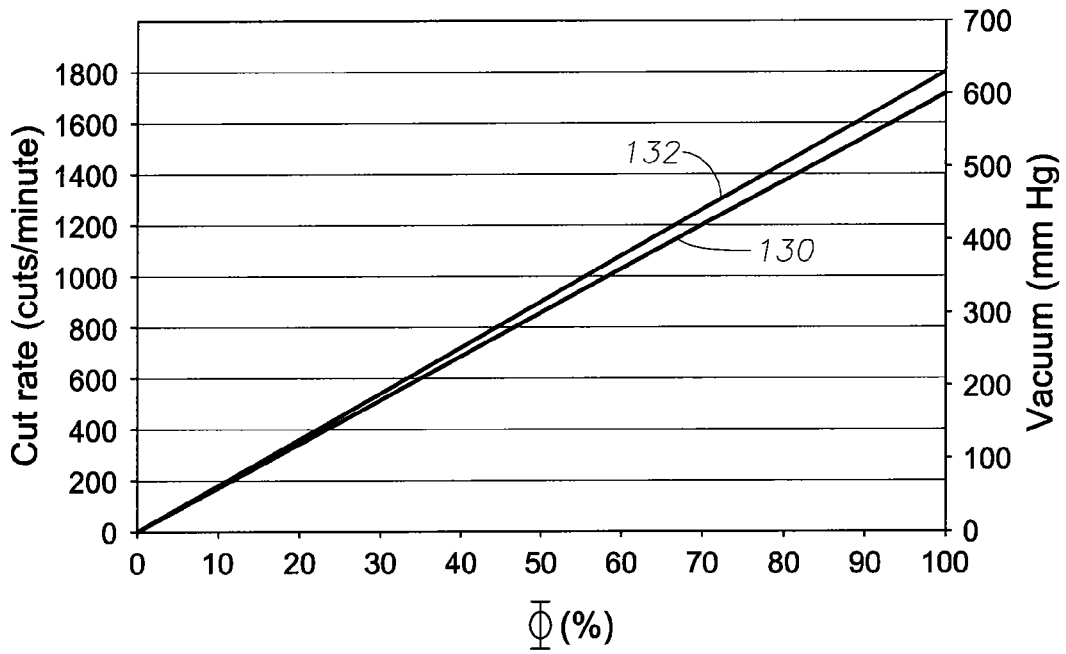
FIG. 6 shows a first preferred, exemplary relationship of cut rate and aspiration vacuum level as a function of the position of the foot pedal of the microsurgical system of FIG. 1.

For example, when system 10 is operating in the posterior segment mode, host module 70 may provide simultaneous, proportional control of both the cut rate and aspiration vacuum level of vitrectomy probe 36 as a function of position Φ. FIG. 6 shows a first preferred relationship of cut rate 132 and aspiration vacuum level 130 of vitrectomy probe 36 as a function of Φ. In FIG. 6, both cut rate 132 and aspiration vacuum level 130 increase linearly with Φ. By providing such simultaneous, proportional control of both cut rate 132 and aspiration vacuum level 140 by simply moving food pedal 52 in a single plane of motion, system 10 eliminates the need for a surgeon to learn and master the complex movements required by traditional approaches of control, and also eliminates the need for a surgeon to utilize a nurse to accomplish such control.

Figure 7:
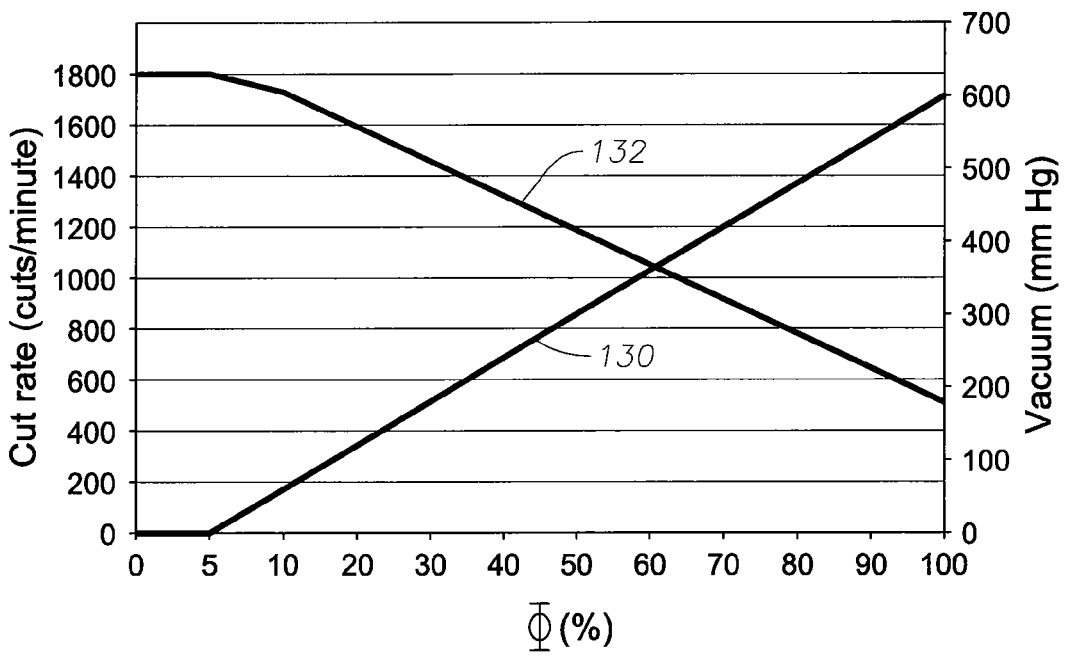
FIG. 7 shows a second preferred, exemplary relationship of cut rate and aspiration vacuum level as a function of the position of the foot pedal of the microsurgical system of FIG. 1.

FIG. 7 shows a second preferred relationship of cut rate and aspiration vacuum level of vitrectomy probe 36 as a function of position Φ. In FIG. 7, aspiration vacuum level 130 generally increases linearly as a function of Φ, and cut rate 132 generally decreases linearly as a function of Φ. More specifically, aspiration vacuum level 130 preferably stays at zero mm Hg for values of Φ from zero to five percent, and then aspiration vacuum level 130 increases linearly with Φ for values of Φ from five to 100 percent. In addition, cut rate 132 preferably stays at maximum value, 1800 cuts per minute, for values of Φ from zero to five percent. Thereafter, cut rate 132 preferably decreases linearly with Φ for values of Φ from five to 100 percent. Stated in another way, cut rate 132 preferably has a "zone of maximum value", and aspiration vacuum level 130 preferably has a "zone of minimum value" for values of position Φ from zero to five percent. The control paradigm of FIG. 7 provides the same benefits to a surgeon as the control paradigm of FIG. 6. In addition, the zone of minimum value for aspiration vacuum level 130 significantly lessens the chance of a surgeon accidentally and suddenly cutting tissue during the surgical procedure. The zone of minimum value allows vitrectomy probe 36 to begin cutting, and for the surgeon to visualize the location of the tip of probe 36 within the eye, before vacuum is supplied to probe 36 causing tissue to be engaged by the probe.

As a second example, when system 10 is operating in the anterior segment mode, host module 70 may provide simultaneous, proportional control of both ultrasound power and aspiration flow rate of ultrasonic handpiece 110 as a function of position Φ. When system 10 is controlled is such a manner, the surgeon is provided with the same functional benefits described above in connection with the control paradigm of FIG. 6. It is also believed that the surgeon is provided with a predictable interaction of both ultrasound power and aspiration flow rate of ultrasound probe 110 that may achieve surgical performance unobtainable by traditional control of one of these variables at a time.

Figure 8:
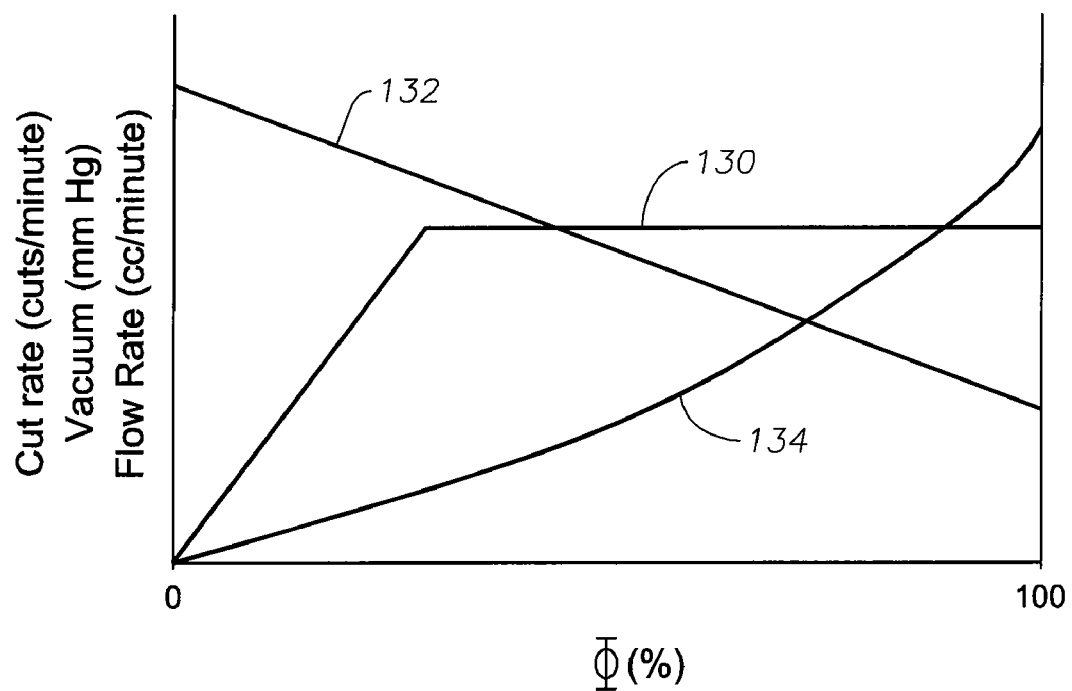
FIG. 8 shows a schematic, exemplary relationship of cut rate, aspiration vacuum level, and flow rate as a function of the position of the foot pedal of the microsurgical system of FIG. 1.

Referring now to FIG. 8, it will be apparent that host module 70, and/or modules 72, 74, 76, and 78, may provide simultaneous, proportional control of two or more surgical parameters of microsurgical system 10, each as a function of position Φ of foot pedal 52, and that such proportional control may be either linear or non-linear. As shown schematically in the control paradigm of FIG. 8, the cut rate 132 of a surgical probe decreases linearly with Φ, and both vacuum aspiration level 130 and flow rate 134 increase in a non-linear manner with Φ. The control paradigm of the present invention may thus be customized for a wide variety of surgical procedures and surgical techniques.

From the above, it may be appreciated that the present invention provides a surgeon with a more flexible, easier to use method of actuating a foot controller to simultaneously control multiple surgical parameters in an ophthalmic surgical procedure. The present invention reduces the level of surgeon dexterity required to simultaneously manipulate two surgical parameters as compared to traditional methods of manipulation. The present invention is easily scalable to the simultaneous control of two, three, or more parameters. The present invention allows for a surgeon to simultaneously vary two or more surgical parameters in a predictable and repeatable manner resulting in optimum and reproducible system performance.

The present invention is illustrated herein by example, and various modifications may be made by a person of ordinary skill in the art. For example, host module 70 may proportionally control two or more surgical parameters of surgical system 10, each as a function of Φ, solely according to pre-defined equations, as described hereinabove. Alternatively, using the touch screen capability of display 16 of system 10, a user may assign the initial values of each surgical parameter when position Φ is zero percent, and/or the final values of each surgical parameter when angle Φ is one hundred percent, and host module 70 may then proportionally control the surgical parameters, each as a function of Φ, according to such user input and pre-defined equations.

It is believed that the operation and construction of the present invention will be apparent from the foregoing description. While the apparatus and methods shown or described above have been characterized as being preferred, various changes and modifications may be made therein without departing from the spirit and scope of the invention as defined in the following claims.

What is claimed is:

1. A method of providing simultaneous proportional control of multiple surgical parameters in an ophthalmic microsurgical system, comprising the steps of:
   providing an ophthalmic microsurgical system, said system comprising:
   a vitrectomy probe;
   a computer;
   a foot controller operatively coupled to said computer, said foot controller having a foot pedal capable of movement in a generally vertical plane of motion between a first end point and a second end point, wherein said first end point is a fully undepressed position of said foot pedal and said second end point is a fully depressed position of said foot pedal, and wherein said movement has a first region between said first end point and an intermediate point and a second region between said intermediate point and said second end point;
   a first surgical parameter, said first surgical parameter being a cut rate of said vitrectomy probe; and
   a second surgical parameter, said second surgical parameter being an aspiration vacuum level of said vitrectomy probe;
   determining a position of said foot pedal between said first end point and said second end point;
   proportionally controlling a value of said first surgical parameter as a function of said position of said foot pedal in said vertical plane of motion; and
   proportionally controlling a value of said second surgical parameter as a function of said position of said foot pedal in said vertical plane of motion simultaneous with said step of proportionally controlling said value of said first surgical parameter and independent of the manner in which said value of said first surgical parameter is proportionally controlled, wherein said first surgical parameter is maintained at a constant maximum value in said first region, said second surgical parameter is maintained at a constant minimum value in said first region, said first surgical parameter decreases in a linear manner in said second region, and said second surgical parameter increases in a non-linear manner in said second region.

2. A method of providing simultaneous proportional control of multiple surgical parameters in an ophthalmic microsurgical system, comprising the steps of:
   providing an ophthalmic microsurgical system, said system comprising:
   a vitrectomy probe;
   a computer;
   a foot controller operatively coupled to said computer, said foot controller having a foot pedal capable of movement in a generally vertical plane of motion between a first end point and a second end point, wherein said first end point is a fully undepressed position of said foot pedal and said second end point is a fully depressed position of said foot pedal, and wherein said movement has a first region between said first end point and an intermediate point and a second region between said intermediate point and said second end point;
   a first surgical parameter, said first surgical parameter being a cut rate of said vitrectomy probe; and
   a second surgical parameter, said second surgical parameter being an aspiration vacuum level of said vitrectomy probe;
   determining a position of said foot pedal between said first end point and said second end point;
   proportionally controlling a value of said first surgical parameter as a function of said position of said foot pedal in said vertical plane of motion; and
   proportionally controlling a value of said second surgical parameter as a function of said position of said foot pedal in said vertical plane of motion simultaneous with said step of proportionally controlling said value of said first surgical parameter and independent of the manner in which said value of said first surgical parameter is proportionally controlled, wherein said first surgical parameter is maintained at a constant maximum value in said first region, said second surgical parameter is maintained at a constant minimum value in said first region, said first surgical parameter decreases in a non-linear manner in said second region, and said second surgical parameter increases in a linear manner in said second region.

3. A method of providing simultaneous proportional control of multiple surgical parameters in an ophthalmic microsurgical system, comprising the steps of:
   providing an ophthalmic microsurgical system, said system comprising:
   a vitrectomy probe;
   a computer;
   a foot controller operatively coupled to said computer, said foot controller having a foot pedal capable of movement in a generally vertical plane of motion between a first end point and a second end point, wherein said first end point is a fully undepressed position of said foot pedal and said second end point is a fully depressed position of said foot pedal, and wherein said movement has a first region between said first end point and an intermediate point and a second region between said intermediate point and said second end point;
   a first surgical parameter, said first surgical parameter being a cut rate of said vitrectomy probe; and
   a second surgical parameter, said second surgical parameter being an aspiration vacuum level of said vitrectomy probe;
   determining a position of said foot pedal between said first end point and said second end point;
   proportionally controlling a value of said first surgical parameter as a function of said position of said foot pedal in said vertical plane of motion; and
   proportionally controlling a value of said second surgical parameter as a function of said position of said foot pedal in said vertical plane of motion simultaneous with said step of proportionally controlling said value of said first surgical parameter and independent of the manner in which said value of said first surgical parameter is proportionally controlled, wherein said first surgical parameter is maintained at a constant maximum value in said first region, said second surgical parameter is maintained at a constant minimum value in said first region, said first surgical parameter decreases in a non-linear manner in said second region, and said second surgical parameter increases in a non-linear manner in said second region.

4. A method of providing simultaneous proportional control of multiple surgical parameters in an ophthalmic microsurgical system, comprising the steps of:
providing an ophthalmic microsurgical system, said system comprising:
an ultrasonic handpiece;
a computer;
a foot controller operatively coupled to said computer, said foot controller having a foot pedal capable of movement in a generally vertical plane of motion between a first end point and a second end point, wherein said first end point is a fully undepressed position of said foot pedal and said second end point is a fully depressed position of said foot pedal, and wherein said movement has a first region between said first end point and an intermediate point and a second region between said intermediate point and said second end point;
a first surgical parameter, said first surgical parameter being an ultrasound power of said ultrasonic handpiece; and
a second surgical parameter, said second surgical parameter being an aspiration vacuum level of said ultrasonic handpiece;
determining a position of said foot pedal between said first end point and said second end point;
proportionally controlling a value of said first surgical parameter as a function of said position of said foot pedal in said vertical plane of motion; and
proportionally controlling a value of said second surgical parameter as a function of said position of said foot pedal in said vertical plane of motion simultaneous with said step of proportionally controlling said value of said first surgical parameter and independent of the manner in which said value of said first surgical parameter is proportionally controlled, wherein said first surgical parameter is maintained at a constant maximum value in said first region, said second surgical parameter is maintained at a constant minimum value in said first region, said first surgical parameter decreases in a linear manner in said second region, and said second surgical parameter increases in a non-linear manner in said second region.

5. A method of providing simultaneous proportional control of multiple surgical parameters in an ophthalmic microsurgical system, comprising the steps of:
providing an ophthalmic microsurgical system, said system comprising:
an ultrasonic handpiece;
a computer;
a foot controller operatively coupled to said computer, said foot controller having a foot pedal capable of movement in a generally vertical plane of motion between a first end point and a second end point, wherein said first end point is a fully undepressed position of said foot pedal and said second end point is a fully depressed position of said foot pedal, and wherein said movement has a first region between said first end point and an intermediate point and a second region between said intermediate point and said second end point;
a first surgical parameter, said first surgical parameter being an ultrasound power of said ultrasonic handpiece; and
a second surgical parameter, said second surgical parameter being an aspiration vacuum level of said ultrasonic handpiece;
determining a position of said foot pedal between said first end point and said second end point;
proportionally controlling a value of said first surgical parameter as a function of said position of said foot pedal in said vertical plane of motion; and
proportionally controlling a value of said second surgical parameter as a function of said position of said foot pedal in said vertical plane of motion simultaneous with said step of proportionally controlling said value of said first surgical parameter and independent of the manner in which said value of said first surgical parameter is proportionally controlled, wherein said first surgical parameter is maintained at a constant maximum value in said first region, said second surgical parameter is maintained at a constant minimum value in said first region, said first surgical parameter decreases in a non-linear manner in said second region, and said second surgical parameter increases in a linear manner in said second region.

6. A method of providing simultaneous proportional control of multiple surgical parameters in an ophthalmic microsurgical system, comprising the steps of:
providing an ophthalmic microsurgical system, said system comprising:
an ultrasonic handpiece;
a computer;
a foot controller operatively coupled to said computer, said foot controller having a foot pedal capable of movement in a generally vertical plane of motion between a first end point and a second end point, wherein said first end point is a fully undepressed position of said foot pedal and said second end point is a fully depressed position of said foot pedal, and wherein said movement has a first region between said first end point and an intermediate point and a second region between said intermediate point and said second end point;
a first surgical parameter, said first surgical parameter being an ultrasound power of said ultrasonic handpiece; and
a second surgical parameter, said second surgical parameter being an aspiration vacuum level of said ultrasonic handpiece;
determining a position of said foot pedal between said first end point and said second end point;
proportionally controlling a value of said first surgical parameter as a function of said position of said foot pedal in said vertical plane of motion; and
proportionally controlling a value of said second surgical parameter as a function of said position of said foot pedal in said vertical plane of motion simultaneous with said step of proportionally controlling said value of said first surgical parameter and independent of the manner in which said value of said first surgical parameter is proportionally controlled, wherein said first surgical parameter is maintained at a constant maximum value in said first region, said second surgical parameter is maintained at a constant minimum value in said first region, said first surgical parameter decreases in a non-linear manner in said second region, and said second surgical parameter increases in a non-linear manner in said second region.

* * * * *